United States Patent [19]
Taba

[11] Patent Number: 5,685,722
[45] Date of Patent: Nov. 11, 1997

[54] ELECTRONIC TIMING SWIMMER'S GOGGLES

[75] Inventor: Serge Taba, Mission Viejo, Calif.

[73] Assignee: U.S. Divers Co., Inc., Santa Ana, Calif.

[21] Appl. No.: 421,831

[22] Filed: Apr. 13, 1995

[51] Int. Cl.⁶ .................................................. G04F 7/10
[52] U.S. Cl. ........................... 434/254; 434/247; 482/3; 482/901
[58] Field of Search ............................... 434/254, 247; 482/1-5, 51, 901; 600/27; 2/426

[56] References Cited

U.S. PATENT DOCUMENTS

| | | |
|---|---|---|
| 3,260,991 | 7/1966 | Laakmann . |
| 3,712,714 | 1/1973 | Uyeda et al. . |
| 3,717,991 | 2/1973 | Klar . |
| 3,797,010 | 3/1974 | Adler et al. ............... 482/51 X |
| 4,285,041 | 8/1981 | Smith ........................ 482/3 X |
| 4,526,036 | 7/1985 | Morrison .................... 482/3 X |
| 4,757,714 | 7/1988 | Purdy et al. . |
| 4,776,045 | 10/1988 | Mysliwiec et al. . |
| 4,796,987 | 1/1989 | Linden . |
| 4,817,633 | 4/1989 | McStrvick et al. . |
| 4,823,367 | 4/1989 | Kreutzfeld . |
| 4,993,004 | 2/1991 | Loizeaux . |
| 5,033,818 | 7/1991 | Barr . |
| 5,124,960 | 6/1992 | Miller et al. . |
| 5,130,955 | 7/1992 | Luerker et al. . |
| 5,136,621 | 8/1992 | Mitchell et al. . |
| 5,162,828 | 11/1992 | Furness et al. . |
| 5,258,785 | 11/1993 | Dawkins . |
| 5,266,977 | 11/1993 | Linden . |
| 5,301,668 | 4/1994 | Hales . |
| 5,391,080 | 2/1995 | Bernacki et al. ............ 482/901 X |
| 5,518,497 | 5/1996 | Widjaja et al. ............. 600/27 |

Primary Examiner—Jerome Donnelly
Assistant Examiner—Glenn E. Richman
Attorney, Agent, or Firm—George F. Bethel; Patience K. Bethel

[57] ABSTRACT

A swimmer's goggles incorporating an electronic timer and display for displaying the times of a swimmer with a display accessible to a swimmer connected to the goggles. An accelerometer is used to determine a swimmer's movement with an electronic circuit for processing the information from the accelerometer to determine a swimmer's movements and time between movements.

23 Claims, 6 Drawing Sheets

IMMOBILE ON PODIUM

START

SWIMMING

FLIP TURN $K_2 = 2$

STOP SWIMMING $K_1 = 3$

ELECTRONIC TIMING SWIMMER'S GOGGLES

BACKGROUND OF THE INVENTION

1. Field of the Invention

The field of this invention resides within the goggles and electronic timing art for swimmers. It specifically resides within the area of electronically timing a swimmer's activity as to laps and total time that the swimmer is swimming, and providing for a display thereof to the swimmer when swimming.

2. Description of the Prior Art

The prior art has many references directed to display systems for timing sporting activity.

U.S. Pat. Nos. 5,162,828 and 4,757,714 are directed to a display system with a head mounted view transparency for displaying information to a swimmer wearing glasses, goggles, or a dive mask. One embodiment is shown with ski goggles having a frame that supports a transparency or a lens. The signal supplied to the display, of the skier's speed, is derived from a sensor and processed by a microprocessor.

When used as a dive mask, the display provides and calculates data and time remaining for a dive, and the air supply, tank pressure, depth of the diver, magnetic heading and other aspects. However, the application of the technology would not be applicable to a swimmer wanting to establish an easily timed laps or multiple lap when swimming.

U.S. Pat. No. 5,136,621 is directed to a non-contact timer counter for use in water for timing a swimmer. A submersible housing with a battery power supply has numerous displays, receivers, and magnetic switches. The housing is placed in the water at the end of a swimming lane and is activated by passing a magnet in proximity to the switch sensing signals coming from the swimmer's transmitter. As can be appreciated, this device is cumbersome and requires increased swimmer bulk and apparatus.

This invention overcomes the foregoing problems. Also, the foregoing patent requires that a transmitter be activated by a mosfet transistor that senses when it enters the water. The sensing of the completion of a lap is by time differentials between the two receivers when a direction is changed. However, the patent does not even remotely teach the invention hereof which is an improved system incorporating an accelerometer and timing method.

U.S. Pat. No. 4,776,045 is directed to a pair of swim goggles with an automatically actuated timing device. In this particular case, the goggles have an eye covering and a timing module attached to one eye covering in a location that is out of the line of sight but in the field of vision. A double convex lens is used to create a virtual image of the timing device.

The operation is such wherein a conductive type of water sensor is provided for automatically starting the timer for a preset count when the device enters the water. However, the timing device is stopped manually and is not automatically provided with signals as in the Applicant's invention hereof which is a distinct improvement over the foregoing patent and prior art both singularly and collectively.

U.S. Pat. No. 4,796,987 describes a stop watch mounted in a lens and goggle's mask or shield for use by a swimmer to observe lapsed time during an activity. The goggles have a stop watch mounted by a sealant in the exterior of a transparent lens. A stop-start and reset button can be fabricated as an integral portion of the goggles 10 but does not incorporate the features of the Applicant's invention hereof as to starting, timing and overall smoothness of operation as to lap timing and total lap time.

U.S. Pat. No. 5,258,785 discloses a data display for sporting eyewear. The patent when specifically applied to swimming goggles has an electronic timing circuit that is actuated by external buttons. The timing functions can be activated and monitored remotely through a radio frequency system as well as having a motion sensitive mercury switch to indicate flip turns. However, the circuit and goggles do not provide the accelerometer functions of the invention. The teachings of the patent particularly do not provide for pulse rate displays and more importantly the measurement of times based upon a swimmer's movements and analysis of such movements such as through a linear regression analysis.

Finally, U.S. Pat. No. 5,124,960 describes a timing device where an input can be provided for the actuation of a pressure transducer. This is effectuated either by a simple motion of the operator or by contact of the operator with another object such as when a swimmer turns against a wall. Here again, the device is complex compared to the Applicant's device as will be seen hereinafter. Also, it does not pertain to the ability of providing timing through an accelerometer principle and method of establishing multiple swimming movements for purposes of timing and display.

The basic concept of the Applicant's invention in providing for information as maintained by a linear regression system and the methodology process of the system of this invention overcomes the deficiencies of the prior art. The Applicant's device incorporates an accelerometer principle to start the timing as well as provide for establishing repetitive movement, respective turns, and the finish. This will be seen from the following aspects of the Applicant's invention incorporating a unique method, an apparatus which is maintained for purposes of timing a swimmer's movements in laps both as to individual laps and the entire race time or swimming time of a swimmer. The invention further provides a timing system for a swimmer's pulse rate.

SUMMARY OF THE INVENTION

In summation, this invention incorporates electronic goggles and a method for timing a swimmer's laps and overall swimming time by means of an electronic accelerometer establishing movement and a method of reviewing that movement as to the swimmers characteristics while in the water, as well as a pulse rate timer.

More specifically, the invention incorporates swimmer's goggles having two lenses and a strap to hold the goggles in place. Within one of the lenses, a battery powered electronic circuit is utilized in a display. The display presents a swimmer's pulse, lap time, and overall time by means of the display that is made visible to a swimmer when viewing the electronic display that is the output of the electronic circuitry and the accelerometer.

The electronic circuitry and method incorporates an accelerometer which establishes the time upon the swimmer making a movement to enter the water. While the swimmer is in the water, moving in a consistent manner, the accelerometer records these movements and establishes by the method of this invention that the swimmer is moving through the water while at the same time timing this movement. Upon the swimmer making a turn, such as a flip turn, or other movement at the end of a lap, the accelerometer records this. This particular movement is then screened with regard to a computational method to assure that the movement is an actual turn.

The timing for each particular lap and overall time is established during these movements and displayed to the swimmer.

After the swimmer has stopped swimming, such as at the end of a race, the accelerometer records a stopping of the swimmer. At such time a check is made to determine that the swimmer has truly stopped. Thereafter, the swimmer is given a display of the entire time of the race or swimming event, and a display of the last lap time of the race.

Concomitant with the timing, is a pulse rate measuring function. The pulse rate measuring function displays the swimmer's pulse rate so as to establish a criteria for the swimmers substantial efforts being undertaken based upon a pre-established pulse rate that the swimmer wants to maintain. Also, an active flashing icon of an analog of the swimmer's pulse rate flashes to indicate a higher or lower rate.

The invention also incorporates a supplemental embodiment incorporating a magnetic wiping switch circuit for determining turns of the swimmer. This is done by a magnetic wiper on a swimmer's arm coming up near a magnetic switch device on the strap of the goggles so as to record a swimmer's arm movement against the strap such as in a flip turn or movement at the end of a lap. This serves to provide for a supplemental check of the swimmer's movements and lap turns.

The foregoing displays are maintained and provided in a sure and facile manner without the requirement of various circuits, stop watches, and other drawbacks of the prior art.

DESCRIPTION OF THE PREFERRED EMBODIMENTS

Figures 1, 2:
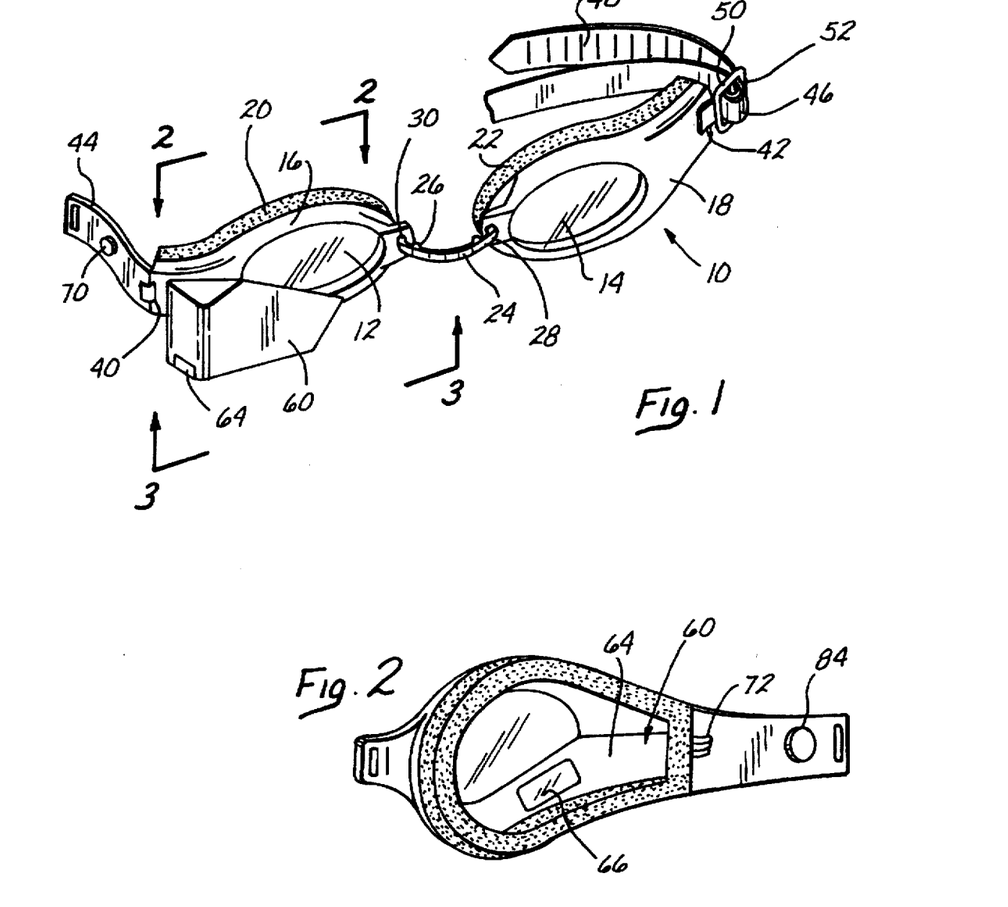
FIG. 1 shows a perspective view of the electronic swimming goggles of this invention.
FIG. 2 is a view looking inwardly toward the goggle's electronic display in the directions of lines 2—2 of FIG. 1.

Looking more specifically at FIG. 1, it can be seen that a pair of goggles 10 are shown. The goggles 10 have a pair of lenses 12 and 14. The lenses 12 and 14 are mounted in an elastomeric material or lens frame portions 16 and 18 so that they can be mounted appropriately for holding and securement to a swimmer's face.

The goggles 10 also incorporate a pair of padded foam elastomeric cushions 20 and 22 which effectively cushion the goggles against a swimmer's face when under tension.

Between the two respective mounting portions for the lenses 12 and 14 is an adjustable nose bridge portion 24. The nose bridge portion 24 has a series of small ridges, lands or crenellations 26 which are known in the art. The crenellations 26 are moved through openings 28 and 30 of the lens frame portions 16 and 18 for adjustment. The crenellations or ridges are secured by each land of the crenellation or ridge moving through and frictionally engaging the openings 28 and 30. This securement by the adjustment means against the lands 26 so that the goggles can be adjusted across a swimmer's nose accommodates various width faces.

Each of the lens frame portions 16 and 18 terminate with strap receiving openings 40 and 42 on either side. The strap receiving openings 40 and 42 receive a first strap portion 44 which bends around in a looped manner through a looped portion 46. The strap has a number of ridges 48 that provide adjustment around a center buckle portion 50 of a buckle 52. Thus, the strap can be oriented inwardly and outwardly for comfort and adjustability of the lenses 12 and 14 mounted in the lens frame portions 16 and 18.

On the right hand lens portion which would be the left hand side in viewing FIG. 1, a plastic electronics case or electronic housing 60 is shown. The electronic housing 60 incorporates the electronics of the system. This is mounted in any suitable manner against the lens frame portion 16 or can be molded into it as part of the lens frame portion.

Figure 3:
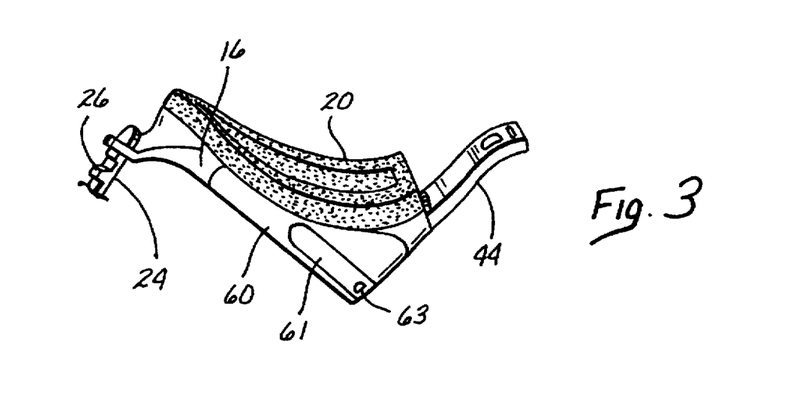
FIG. 3 is a view looking upwardly in the direction of lines 3—3 of FIG. 1.

The electronics housing 60 also incorporates a battery insertion pocket with a battery housing slide portion 61 that can be seen more clearly in FIG. 3 having a little tab 63 for a removal of the battery slide portion 61. Thus, batteries can be changed easily by merely sliding the slide portion 61 outwardly and exchanging a depleted battery for a new battery.

Looking more particularly at FIGS. 2 and 3 it can be seen that the showing of FIG. 2 indicates the electronics housing 60 which has been provided with a beveled appearance with a face 64 mounting a display 66. The display 66 can be seen in FIG. 4 and will be described in greater detail hereinafter.

The electronic housing 60 mounting the electronics incorporates a capability of initiating or starting the electronics by means of an initialization and reset button 70 that can be pressed to initiate the electronics. The button 70 is connected through wire leads or wiring 72 to the electronics housing 60 as seen in greater detail in FIG. 2.

The showing of FIG. 2 also indicates a protrusion forming a pulse sensing button 84 which serves as a pulse sensing device. Fundamentally, the pulse sensing device 84 merely senses near the temple of a swimmer the pulses to provide for a display of the pulse rate. This can be in the form of any transducer which receives pulse movements of a swimmer and then can transmit them through the wiring 72 to the electronics in the housing 60.

Figure 4:
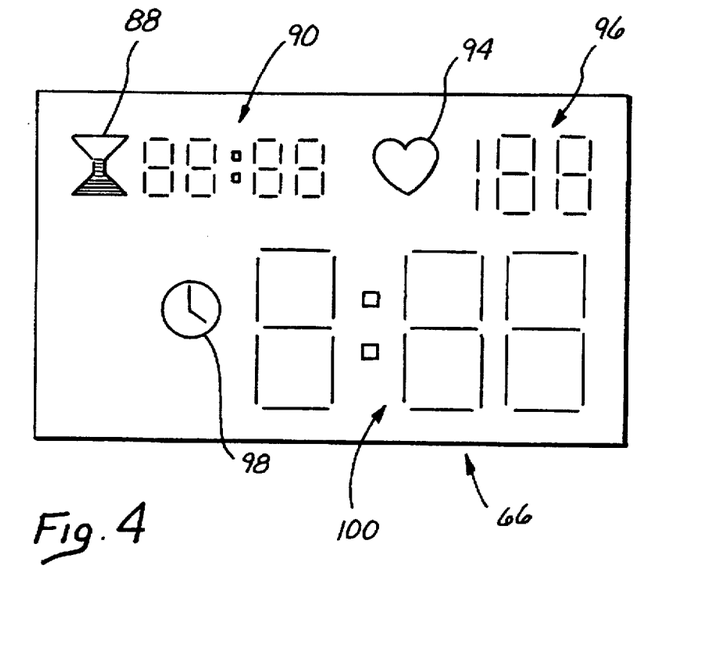
FIG. 4 is a view of the display as seen within the interior of the showing of FIG. 2.

The display 66 as shown in greater detail in FIG. 4 includes a fixed icon 88 for indicating time. The icon 88 is a fixed icon which gives the swimmer the capability of determining the particular display which is displayed to the right as seen in FIG. 4. The display to the right indicates the total time through the display seen as the time display readout 90 which includes both the minutes and the seconds split by the normal colon. The time display readout 90 can be of any suitable type which is known in the art including those displays which incorporate a seven bar numeric display function known in the art for liquid crystal displays or other lighted displays.

A second icon 94 is next to a pulse rate timer display 96 which has three seven bar figure displays for indicating a pulse rate. The icon 94 can be an LED or other lit display with a driver to cause it to flash. The flash rate is related to the pulse rate and increases or decreases as an analog function of the pulse rate.

The display 66 further includes a lap time icon 98 which is next to a seven bar figure display with three numerals showing the lap time. This is shown by a lap time display function 100 which is a major display which incorporates the lap time so that it reads out in minutes and seconds.

These particular displays and functions will be more readily understood when the circuitry hereinafter is enunciated as to the block diagram and the method for timing a swimmer's moves.

Figure 5:
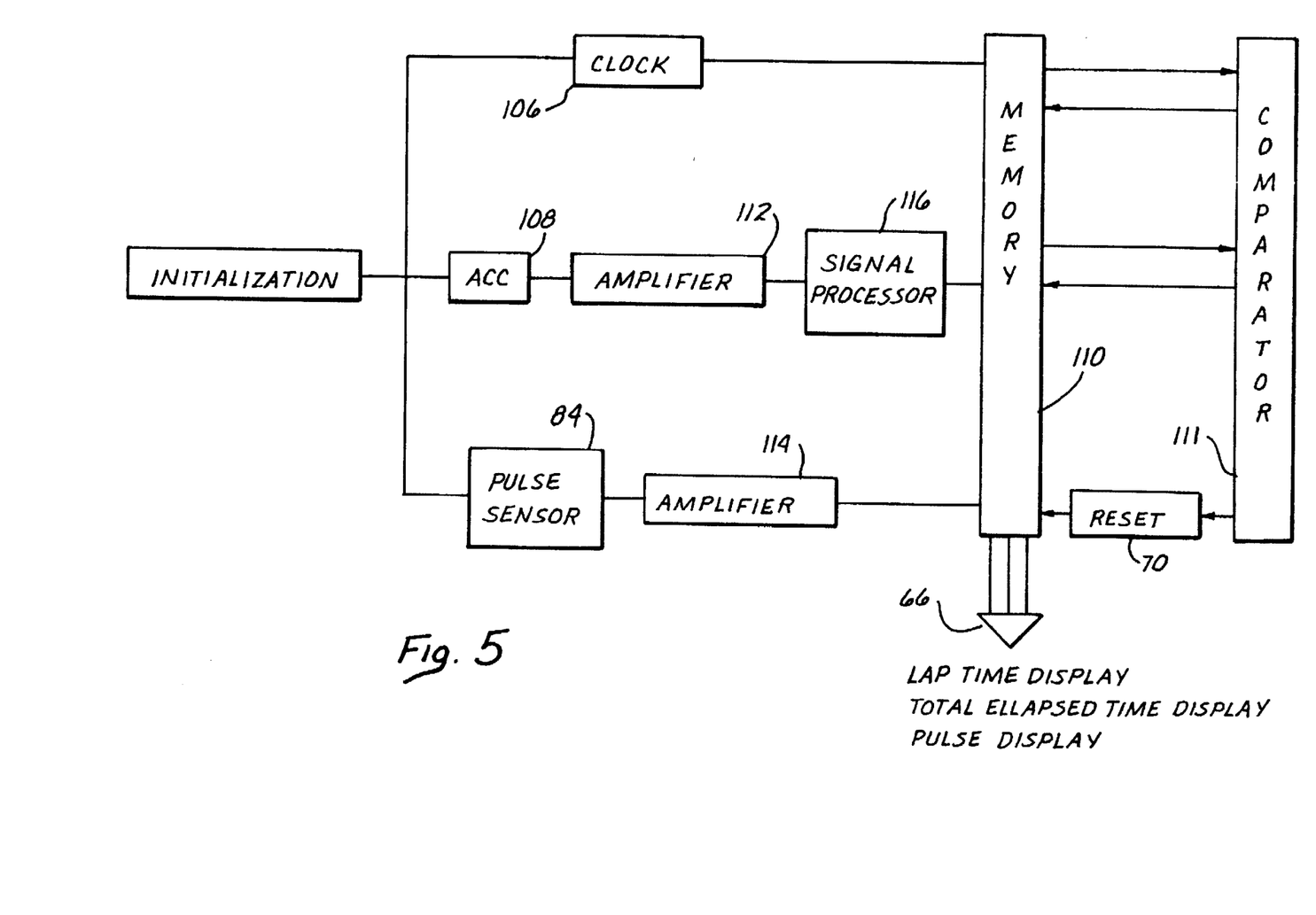
FIG. 5 is a block diagram of the circuitry of this invention and the method by which laps are recorded.

Looking more particularly at FIG. 5, it can be seen that a block diagram is shown that outlines the macro functions of the invention hereof. Initially, the electronics must be reset and started by the reset button 70 providing for the initialization of the electronics. The initialization then starts the internal clock 106, as well as the pulse sensor which is part of the pulse sensing button 84.

Upon initialization, an accelerometer within the electronic circuit is also started. This accelerometer is seen as accelerometer 108 and is abbreviated in the drawing and graph as Acc. The accelerometer (Acc) can be such wherein it is a piezoelectric, or other type of electronic sensing device which senses accelerated or other types of movements. Such accelerometers are known to provide movements in the X, Y and Z axes. These movements can be responsive to plus or minus movements in the form of signals corresponding to plus or minus X, Y, or Z axis movements.

For instance if an accelerometer switch has a cubic formation opposite faces can provide for plus or minus signals, indicating relative movements in the direction of one face or the other. These six respective cube faces can provide orientations and signals respectively for plus or minus X, Y, and Z movements. The signals can then be processed to indicate movements of gradation both vectorially and otherwise so that a swimmer's movements can be sensed.

The accelerometer 108 and clock 106 are all connected to a memory 110.

Both the accelerometer and the pulse sensor 84 and 108 are provided with amplifiers respectively 112 and 114. The amplifiers 112 and 114 send a signal to the memory 110. However, before the accelerometer signal is sent to the memory, it is processed by a signal processor 116. The signal processor 116 fundamentally takes the wave form that it receives and shapes it so that it can be properly processed by the memory. In effect, accelerometers if they do not have a particularly sharp wave form output must have the output shaped into a square wave form for a true digital output.

The memory 110 provides the lap time display, a total elapsed time display and the pulse display in the form of a display 66 as previously set forth. In order to provide this display, a comparator 111 of the accelerometer's 108 output function as will be detailed hereinafter is utilized. The accelerometer's 108 output is that of the plus or minus axial movements related to the three axes X, Y and Z.

The comparator 111 is tied into the memory 110 so that it compares the particular movement of a swimmer. Basically, the comparison is as to the movement of a swimmer from the start after initialization by the reset button 70.

When the swimmer first initializes the electronics, the accelerometer 108 is in a quiet mode due to the fact that the swimmer has not taken off from the side of the pool. At this time the pulse display 96 is providing a numerical readout, and the pulse icon 94 is flashing a signal which is analogous in time to the swimmer's relative pulse rate.

Upon taking off from the side of the pool, the accelerometer 108 immediately responds so that the movement is established within the comparator 111 and the memory 110 to create a situation wherein total timing initially starts. The lap time is not displayed until a time has been reached which is a pre-determined time $t_\alpha$. This time $t_\alpha$ is set to let the swimmer establish his cruise or consistent swimming movements. In effect, the accelerometer movements fall into a consistent series of patterns as an analog of swimming movements as to the X, Y, and Z axes.

The movement of a swimmer is generally in a consistent manner from one end of the pool to the other. As a consequence, the accelerometer 108 records a number of movements and the comparator when checking the memory establishes that the movements are the same through a series of linear regressions.

Upon the swimmer arriving at the end of the pool in order to make a turn, the accelerometer 108 is then changed insofar as its acceleration components that it senses because of the momentary change of movement of the swimmer and the reverse movement. At such time, the comparator 111 compares the movement and rechecks it through a linear regression and then through the memory 110 establishing the movement. The lap time display is then stopped on the lap time display 100. Fundamentally, the lap time is frozen until the pre-determined time $t_\alpha$ is reached during the next lap. In effect $t_\alpha$ is set to assure that the swimmer has established his cruise or generally consistent swimming pattern after each lap in order to display the proper lap time.

The swimmer continues to swim in the same manner so that the linear regressions establish and check the movement of the swimmer during the second and succeeding laps.

This process is continued until the swimmer stops at which time the accelerometer 108 is completely stopped and a check is made as to the information in the memory 110 by the comparator 111. The swimmer's movement is established as to the swimmer absolutely stopping. The timing at that moment, and a true end of the race time is established through a multiple check at which time a calculation is made for providing the entire time. Also the last lap time is displayed on the lap time display 100 of the race which is displayed in the total time readout 90.

Figure 6:
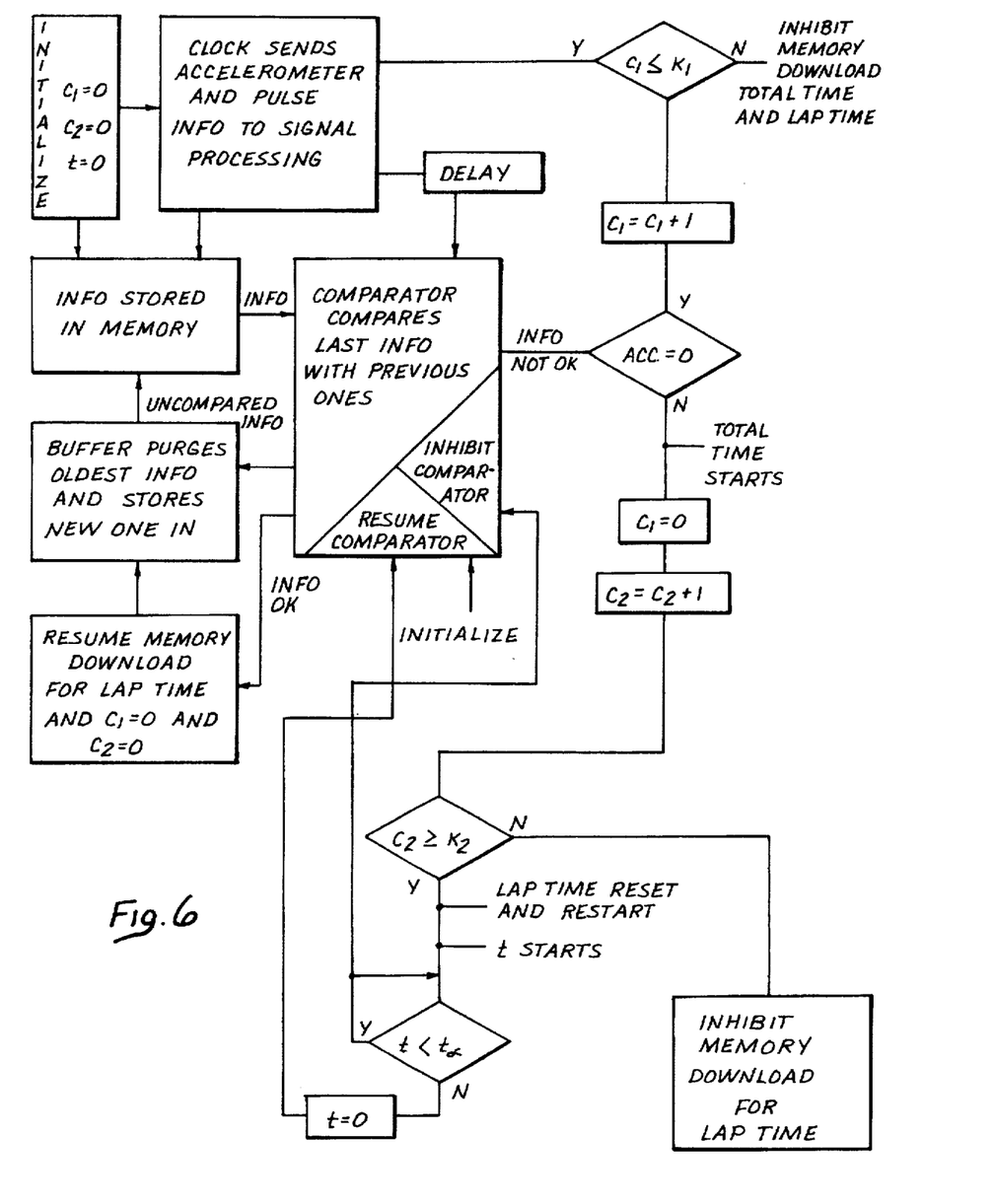
FIG. 6 is a block diagram showing the method and functions of the circuit.

These functions can be more readily understood when reviewing the circuit block diagram seen in FIG. 6. Values C and K for processing the data of the linear regressions are shown as well as N and Y respectively standing for no and yes equivalents.

When looking at FIG. 6 in greater detail, it can be seen that the block diagram therein describes the operation. Fundamentally, when the swimmer is immobile on the podium he initializes the circuitry with the button 70 to start the electronics. At this time, all of the memory and sensors are at zero. The internal clock sends sampling accelerometer 108 pulse information to a signal processor which transforms that information into a positive value. This value is then stored in memory and the pulse value is displayed in the goggles on the display 66 in particular, that portion of pulse rate timer display 96.

The accelerometer 108 is at zero or proximate to zero before the swimmer dives in. The comparator 111 after a delay compares that information with whatever information has been stored in the memory 110 from the initial start. The comparator 111 compares a zero with a series of zeros or proximate zero values. Every time new information is analyzed it is stored in the memory. The oldest information is purged when the new information is stored.

When the swimmer jumps off the podium, the accelerometer 108 is sending information different than the zero or proximate zero information. This initiates the total time and the lap time being started. During a predetermined time $t_\alpha$ the comparator 111 is inhibited from all comparison. The computer or microprocessor is storing information in the memory 110 and creating the pattern for accelerometer 108 analysis. In effect, the movements of the swimmer are determined so that the accelerometer 108 movements are compared as to the initial start, the consistent movement or cruise movement of swimming, the flip turns, and the stopping of the swimmer. As an aside, the comparator 111, memory 110, and numerous other functions except in some cases the accelerometer 108 can be included in one integrated circuit.

During the swimming time, the comparator 111 uses a mathematical algorithm to decide if the new accelerometer 108 information belongs to the pattern. For instance, during the swimming pattern the swimmer would be swimming more or less consistently. If one set of information within the processor analysis as to the next set of information varies, the comparator 111 and memory 110 holding the former information know that a significant event has taken place such as a flip turn or stopping. The flip turn of course is the specific timing event between laps.

If the set of the information belongs to the pattern, the comparator 111 assumes the previous set was an aberration if it is not more than a given value. In this particular case, it has been shown as $C_2$ equalling 1. If predetermined consecutive sets of information represented as $K_2$ do not belong to the previous pattern, the comparator 111 assumes the swimmer is doing a flip turn or has finished the race.

When the swimmer is doing a flip turn, as soon as the comparator 111 has identified that the $K_2$ consecutive sets of information do not belong to the pattern through an analysis with the linear regression, the memory 110 used by the display to show the lap time information does not receive any new information. At this time, the display shows during the time $t_\alpha$ the last lap time set of information stored in memory.

When looking at the block diagram of FIG. 6 it can be seen where these functions are started by the clock maintaining the accelerometer 108 and pulse information for signal processing. This information is sent to the memory 110 and stored therein.

A delay function is provided for storing before the comparator 111 so that proper information is received by the comparator for comparison to the last information. In order to provide for the new information, a buffer purges the oldest information and stores the new information. To this extent, the comparator 111 sends the information to the buffer and states that the information is true information such as the true information of a swimmer in a continuous mode until a flip turn or stopping.

When the information is not considered to be true, and the accelerometer 108 is at zero or proximate to zero as shown in the acc=0 block, it puts out a yes (Y) or no (N) signal. The yes signal goes to the recorder to show that $C_1=C_1+1$. When this particular value is equal to or greater than $K_1$, the display 66 time is stopped and shows the total time 100 and the last lap time.

The $C_1=C_1+1$ calculation is the recorder for the entire race. The $C_2=C_2+1$ calculation is the information required for a flip turn. For the entire race when $C_1+1$ is equal to or greater than $K_1$ the display stops and the total time and lap time are displayed. When $C_2$ is greater than or equal to $K_2$ the lap time has started. These particular functions as to initialization and $t_\alpha$ being the time delay to establish the new pattern of the information being received go to the processor for providing information for the comparator and the information stored in the memory that allows for the verification of the swimmer's movement being established through the linear regression or constant analysis of the accelerometer 108.

The accelerometer 108 establishes start information by starting when the swimmer jumps in. It also establishes continuous information of the swimmer's movement, flip turn information when the swimmer discontinues movement to undertake a flip turn and static movement when the swimmer comes to a stop.

Figure 9:
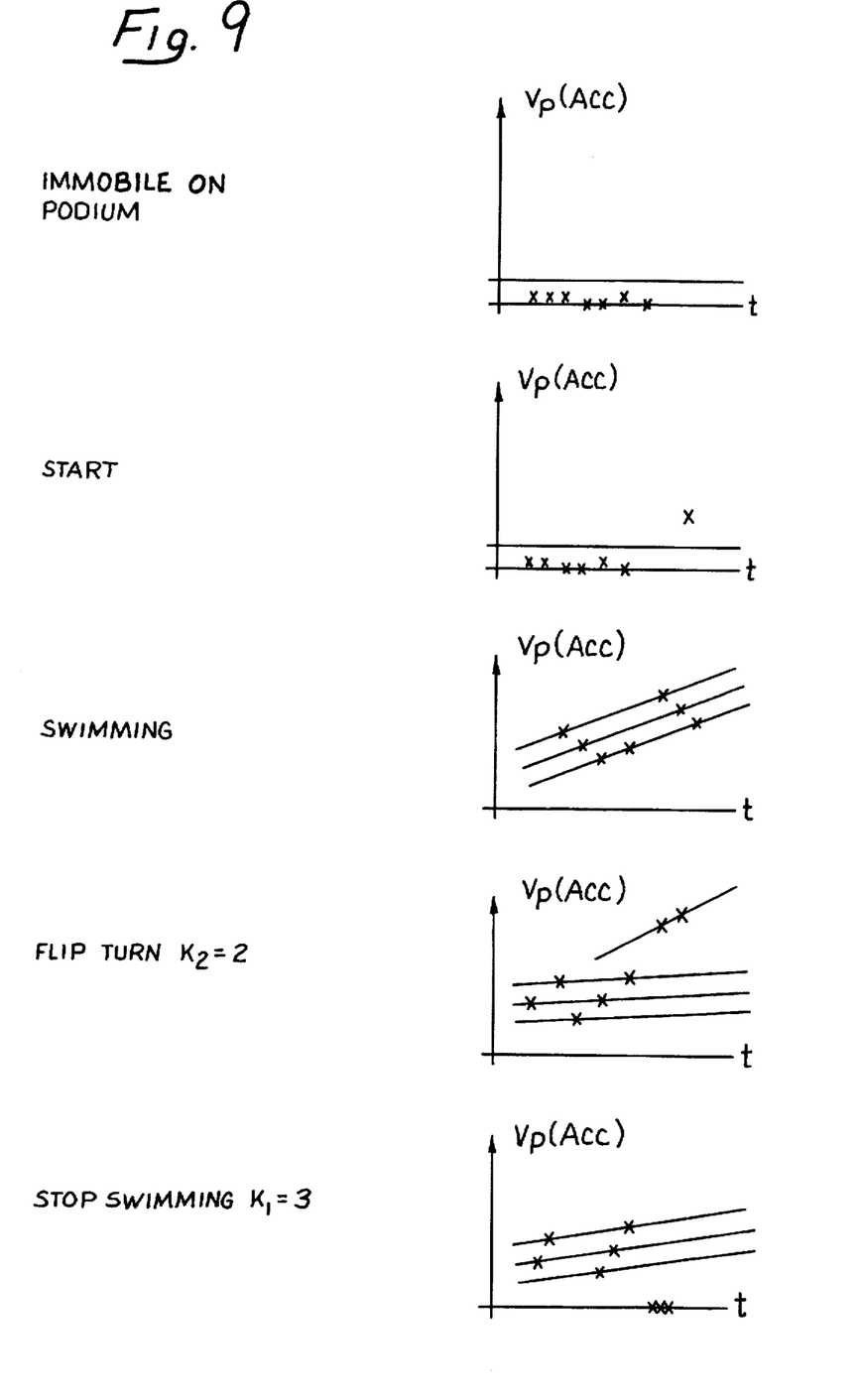
FIG. 9 shows a time line (t) $V_p$ accelerometer (Acc) comparison which is the basis of the comparator review of a linear regression.

A review of FIG. 9 shows a time line (t) $V_p$ accelerometer (Acc) comparison which is the basis of the comparator review for the linear regression.

As can be seen in FIG. 9, when the swimmer is immobile on the podium during a prescribed period of time the accelerometer 108 provides on a time line t little or no change (i.e. zero or proximate zero). In effect any accelerometer 108 changes are not significant as being below a proximate zero, or preestablished Acc value line. This line is above the line t. Upon the start, the accelerometer 108 shows a movement by showing the acceleration $V_p$ above the zero acceleration line and above the proximate zero movement line which is pre-set as to parameters for accelerometer movement.

During swimming, consistent movement of the accelerometer 108 shows continuity over the time line t. At the moment of the flip turn, the accelerometer 108 changes so that an aberration takes place and the movement changes. If at such point $K_2=2$ it will recognize the flip turn and it will display the lap time on the display 100. The recording of the lap times continues with $K_2=2$ to record each lap.

When swimming is stopped the accelerometer 108 on the time line is shown as providing zero or limited acceleration. If at this point $K_1=3$ the total time and the last lap time are displayed on the display 90.

Figure 7:
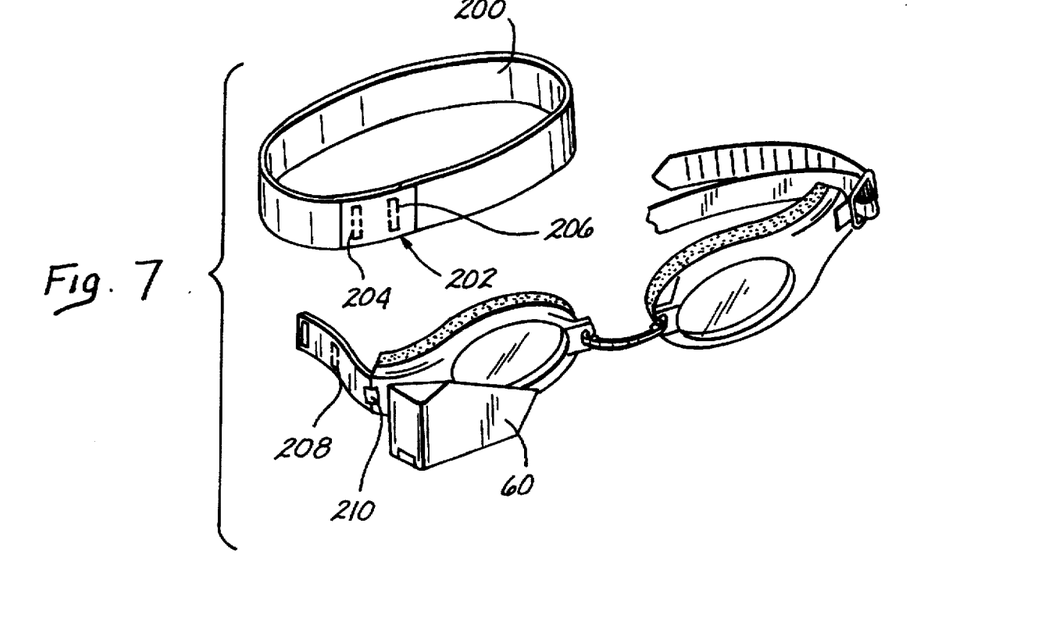
FIG. 7 is a view of an alternative embodiment of this invention incorporating a magnetic switch and wiper.

In some cases, it is believed that the accelerometer principle can be enhanced or a different embodiment can be utilized by incorporating the functions of an arm band and magnetic switch. This is shown in FIG. 7. In FIG. 7 an arm band 200 is shown which goes around a swimmer's arm. The arm band 200 can be of any type of material such as a relatively soft elastomeric material. Attached to the arm band is a magnetic wiper 202 having two magnets 204 and 206. The magnets 204 and 206 serve to wipe against or be in proximity to a magnetic switch 208 which is connected by wires such as those at a hinge point 210 to the electronic housing 60.

The principle of operation is that when a swimmer does a flip turn in order to have a positive lap timing, the arm band 200 can be brought up and wiped across or placed in proximity to the magnetic switch 208 in order to provide an input to the electronics in the housing 60. This will then provide for an absolute display at the time when provided to the memory and comparator of the circuitry which can then be displayed on the lap time display 100.

Figure 8:
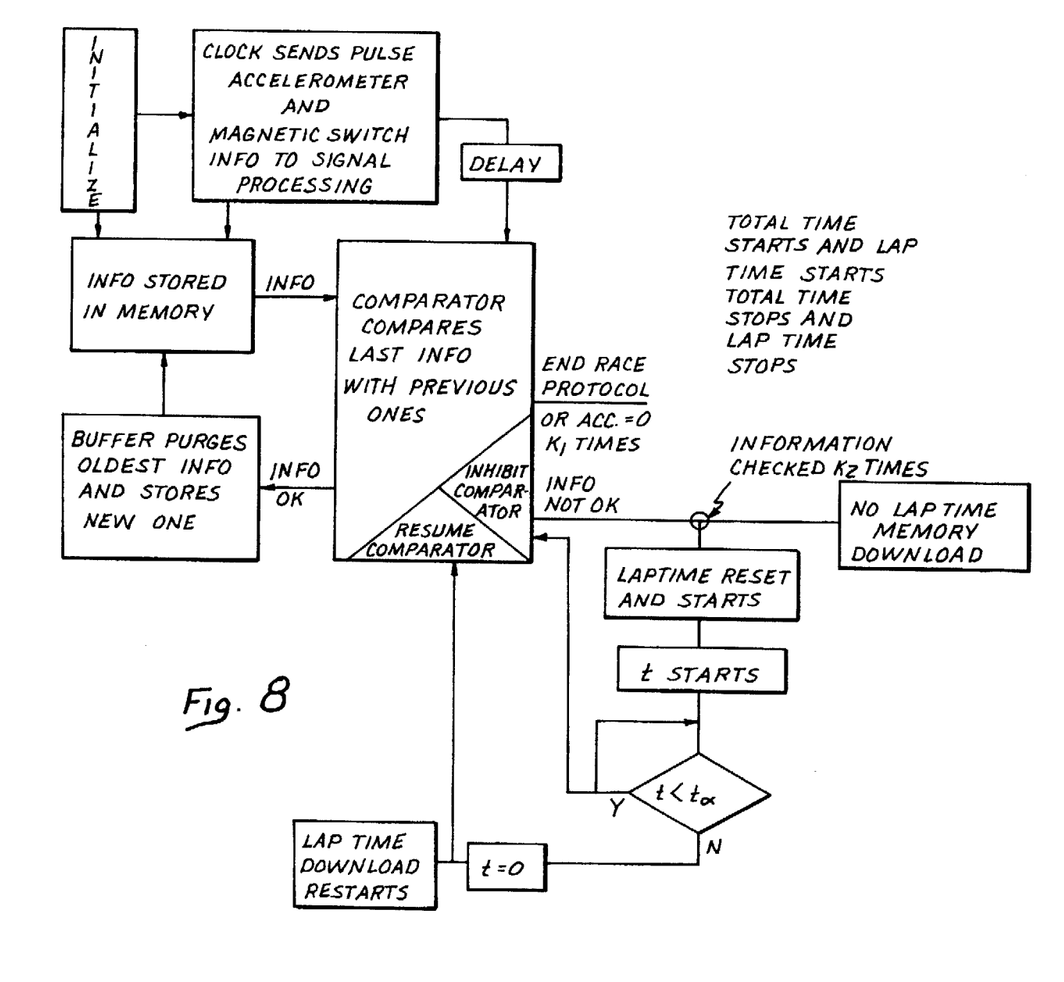
FIG. 8 is a block diagram and method incorporated with the magnetic wiper of FIG. 7.

In order to understand the functions of the magnetic wiper, it can be seen in FIG. 8 that the initialization is started again by the initialization function of the button 70. At this time, the clock sends accelerometer 108 and magnetic switching information from the switch 208 for signal processing. This is sent to the memory and a pulse signal to the comparator compares the last information with the previous one in the linear regression system as previously described. The information is also sent through a delay to the comparator. As in the previous embodiment, a buffer purges the oldest information and stores new information.

When the accelerometer 108 is no longer indicating zero, the total time starts and lap time starts. The end of the race protocol of course will again show an accelerometer 108 reading within the parameter of zero or proximate to zero as established on the Acc value line. As in the prior case it will be reviewed $K_1$ times to assure that the information is accurate.

The magnetic switch 208 causes a logging of information and provides for lap time resets and starts. When the time is less than $T_\alpha$ the buffer only is being supplied with data. Thereafter the comparator analysis the information and checks to see if it is a flip turn (i.e. $K_2$=2) or the end of the race (i.e. $K_1$=3).

The foregoing describes the invention such that an accelerometer can be used to determine the start of a swimmer's race, the turns, and the end of the race providing for lap time, total time and pulse rate. This entire system can be enhanced by means of the magnetic switching system as shown in FIG. 7 to assure that the flip turns are recorded without any aberrations and that the linear regression establishing the movement of the swimmer establishes true movement by a swimmer recording the data after one or two linear regressions of the accelerometer information to provide proper information for lap time and total time.

I claim:

1. A swimmer's goggles incorporating an electronic timer and display for displaying the times of a swimmer comprising:

a pair of goggles having at least one lens therein;

a display means accessible to a swimmer connected to said goggles;

accelerometer means to determine a swimmer's movement; and, an electronic circuit for processing information from said accelerometer means to determine a swimmer's movements including a memory and comparator circuit connected to said accelerometer means for comparing movement based upon the information in said memory, and said memory is connected to said display means for showing a calculated lap time.

2. The goggles as claimed in claim 1 further comprising: means to initiate said electronic circuit.

3. The goggles as claimed in claim 2 further comprising: an electronic circuit for measuring the time from an initial accelerometer means movement to a second accelerometer movement.

4. The goggles as claimed in claim 3 further comprising: means to determine swimming movement when said accelerometer means is recording continuity of movement of the swimmer in the water.

5. The goggles as claimed in claim 1 further comprising: circuit means to provide for a linear regression review of a swimmer's movements after an initial start so as to indicate continuity of movement until the swimmer has discontinued such movement.

6. The goggles as claimed in claim 3 further comprising: means for displaying time to a swimmer of said second movement.

7. The goggles as claimed in claim 1 further comprising: circuit and display means to indicate when accelerometer movement has stopped.

8. The goggles as claimed in claim 1 further comprising: said memory is connected to said display means for showing total time based upon timing between initial accelerometer means movement, continuous accelerometer means movement to a second non-continuous accelerometer means movement indicating laps which are then added together as to time to provide total time after said accelerometer means movement has stopped.

9. The goggles as claimed in claim 1 in combination with: magnetic means for connection to a swimmer's body; a magnetic switch that is actuated upon movement of said magnetic means; and, circuit means for indicating when said magnetic switch is actuated by said magnet means.

10. The goggles as claimed in claim 1 further comprising: a signal processor connected to said accelerometer means for purposes of shaping the signal output of said accelerometer means.

11. A pair of goggles with an electronic timer and display comprising:

a pair of goggles which have lens means therein for a swimmer to look through;

an electronic circuit having a display connected thereto for displaying information to a swimmer which the swimmer can view;

an accelerometer means connected to said circuit for detecting movement of the swimmer;

means for comparing the movement of the swimmer;

means within said circuit for processing said movement so as to indicate starting movements, turning movements and continuous movements of said swimmer as reflected by the movement of said accelerometer means.

12. The goggles as claimed in claim 11 further comprising:

a memory within said electronic circuit for establishing the times of accelerometer means movement; and, comparator means for comparing said information in said memory means as to continuity and changes.

13. The goggles as claimed in claim 12 further comprising:

means for initializing the timing by said electronic circuit and said accelerometer means.

14. The goggles as claimed in claim 13 further comprising:

circuit means for comparing information received from said accelerometer means with previous information; and, means for displaying said information as a function or time after said information has been checked as to continuity.

15. The goggles as claimed in claim 11 further comprising:

circuit means which measure the time of a swimmer starting by said accelerometer means moving from a start position;

circuit means for comparing continuity of movement during a swimmer's swimming movement;

circuit means for comparing accelerometer movement at a turn; and, circuit means for detecting when said accelerometer movement is changed to provide lap times on said display and total time based upon said initial movement, turn movements and stopping movement reflected by said accelerometer means movement.

16. The goggles as claimed in claim 11 further comprising:

means on said goggles for sensing a swimmer's pulse; and, electronic means for displaying said pulse time.

17. A method for measuring a swimmer's lap time and total time comprising:

providing goggles to a swimmer;

providing an electronic circuit means with a display for view by a swimmer;

providing accelerometer means connected to said circuit means;

detecting movement of said accelerometer means;

processing said movements for purposes of establishing a swimmer's time, and;

establishing the start of a swimmer by said accelerometer means initially moving.

18. The method as claimed in claim 17 further comprising:

establishing a swimmer's turn after a swimmer's movement through said accelerometer means moving beyond a repetitive movement.

19. The method as claimed in claim 1 further comprising:

measuring a swimmer's lap time from the stop of movement by said accelerometer means through a linear regression review of a swimmer's consistent movement; and, displaying when said movement has been altered by a difference in movement from said consistent movement.

20. The method as claimed in claim 19 further comprising:

stopping accelerometer means movement to establish the end of a swimmer's movement; and, displaying the time between said initial movement and said stopping of said movement.

21. The method as claimed in claim 17 further comprising:

placing a pulse responsive signal output means in juxtaposition to a swimmer's body;

sensing the pulse of the swimmer; and, displaying said pulse signal as a function of time in a display associated with said swimmer.

22. The method as claimed in claim 17 further comprising:

storing said accelerometer means movement and comparing said accelerometer means movement for purposes of establishing timing of a swimmer.

23. The goggles as claimed in claim 1 further comprising:

means on said goggles for sensing a swimmer's pulse; and electronic means for displaying said pulse time.

\* \* \* \* \*